(12) United States Patent
Maroney et al.

(10) Patent No.: US 6,277,123 B1
(45) Date of Patent: Aug. 21, 2001

(54) PROSTHESIS POSITIONING APPARATUS AND METHOD FOR IMPLANTING A PROSTHESIS

(75) Inventors: Brian J. Maroney, Fort Wayne, IN (US); Charles A. Rockwood, Jr., San Antonio, TX (US); Reese K. Myers, Warsaw, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/394,557

(22) Filed: Sep. 10, 1999

(51) Int. Cl.[7] ................................................ A61B 17/90
(52) U.S. Cl. ............................................ 606/102; 606/99
(58) Field of Search ................................ 606/53, 54, 86, 606/87, 88, 89, 99, 102; 623/19, 22

(56) References Cited

U.S. PATENT DOCUMENTS

| | | |
|---|---|---|
| 5,171,324 | 12/1992 | Campana et al. . |
| 5,951,564 | 9/1999 | Schroder et al. . |
| 5,961,555 | 10/1999 | Huebner . |
| 6,102,953 | 8/2000 | Huebner . |
| 6,168,627 | 1/2001 | Huebner . |
| 6,168,628 | 1/2001 | Huebner . |
| 6,193,758 | 2/2001 | Huebner . |

FOREIGN PATENT DOCUMENTS

| | | |
|---|---|---|
| 298 05 703 U | 8/1998 | (DE) . |
| 2 770 128 A | 4/1999 | (FR) . |
| 747 876 A | 4/1956 | (GB) . |
| WO 97 27828 | 8/1997 | (WO) . |

OTHER PUBLICATIONS

TORNIER Shoulder Prosthesis Aequalis fracture jig brochure, Jun./1995.

*Primary Examiner*—David O. Reip
(74) *Attorney, Agent, or Firm*—Maginot, Addison & Moore (57) ABSTRACT

An apparatus for positioning a prosthesis in a bone includes a body, first and second clamps, a depth gauge and a guide. The first clamp is coupled to the body. The depth gage is coupled to the body and is movable relative thereto generally perpendicular to the shaft of the bone. The second clamp can be selectively engaged with and disengaged from the depth gage. The second clamp is movable with the depth gage and is also moveable in a direction generally parallel to the axis of the bone The guide is used to determine the proper rotational orientation of the apparatus. The first clamp is then secured to the bone. The second clamp is secured to a trial prosthesis and is engaged with the depth gage as the trial is inserted into the bone. When the proper insertion depth is reached, the second clamp is secured to the depth gage. The joint is then reduced and the range of motion checked. The depth and rotational orientation may be adjusted as needed. The second clamp is released from the trial, the trial is removed and the prosthesis is inserted in the bone and secured to the second clamp.

45 Claims, 5 Drawing Sheets

PROSTHESIS POSITIONING APPARATUS AND METHOD FOR IMPLANTING A PROSTHESIS

BACKGROUND AND SUMMARY OF THE INVENTION

The present invention relates to a device for positioning a prosthesis in a bone and a method of implanting a prosthesis.

Various prostheses are known for replacing all or part of a damaged or diseased joint. For example, prostheses for replacing all or a portion of a damaged or diseased knee, hip and shoulder of a person are well known. Often, the joint is replaced by securing one portion of the prosthesis to one bone of the joint and another portion of the prosthesis to another bone.

When reconstructing damaged or diseased joints with artificial prostheses, it is desirable to position the components of the prosthesis such that the structure and function of a properly functioning natural joint is replicated to the greatest degree possible. This involves consideration of several factors. For example, the components of the prosthesis must be inserted such that the patient has the desired limb length after the surgery. It is also desirable that the range of motion of the joint postoperative is, to the extent possible, the same as that of a healthy joint. Some of the factors relevant to proper placement include insertion depth of the prosthesis components into the bone and rotational orientation of the prosthesis components.

The present invention provides an apparatus for positioning a prosthesis in a bone. According to one embodiment of the invention, an apparatus for positioning a prosthesis having a stem in the intramedullary canal of a bone includes a body, a first clamp connected to the body for engaging the bone, a depth gage connected to the body for determining the depth of the prosthesis stem within the intramedullary canal, and a second clamp connected to the depth gage for engaging the prosthesis. The body may include a projection for stabilizing the apparatus when the first clamp engages the bone. A plurality of markings may be provided on the depth gage. The apparatus may include a guide for determining proper rotational orientation of the apparatus relative to the bone. The guide may be selectively secured to and removed from the body. The second clamp may be movable relative to the first clamp. The depth gage may be movable with respect to the first clamp and/or the body. The second clamp may be movable relative to the depth gage. The body may be provided with a channel and the depth gage may be connected to a base that is movable within the channel. The base may include a slot and the channel may include a stop for limiting movement of the base in the channel. The second clamp may be removable from the depth gage and may be engaged with the depth gage in at least two orientations. A cam may be provided for adjusting the first clamp. In one embodiment, the first clamp includes a pair of jaws that engage the shaft of the bone after the soft tissue is removed.

In another embodiment of the present invention, an apparatus for positioning a prosthesis having a stem in the intramedullary canal of a bone having a shaft includes a body, a first clamp for engaging the bone, the first clamp being coupled to the body, a depth gage for determining the depth of insertion of the prosthesis stem in the intramedullary canal, the depth gage being coupled to the body and moveable relative to the body in a direction generally perpendicular to the shaft of the bone, and a second clamp for engaging the prosthesis, the second clamp being coupled to the depth gage for movement therewith and being movable relative to the body in a first direction generally parallel to the shaft of the bone.

According to another embodiment of the present invention, an apparatus for positioning a prosthesis having a stem in the intermedullary canal of a bone includes first means for selectively attaching the apparatus to the bone, second means for determining the depth of insertion of the prosthesis stem in the intramedullary canal, the second means being coupled to the first means, third means for selectively engaging the prosthesis, the third means being coupled to the second means, fourth means for permitting movement of the third means relative to the first means in a first direction, and fifth means for permitting movement of the third means relative to the first means in a second direction. The first means may include a clamp and a cam for operating the clamp. The second means may include a post, which may include at least one marking. The third means may include a clamp. The fourth means may include a post and an opening in the third means that engages the post. The fifth means may include a body moveable within a channel and the third means may be coupled to the body. The apparatus may also include a stop in the channel for limiting movement of the body.

According to another embodiment of the invention, a method of implanting a prosthesis having a stem in the intramedullary canal of a bone includes the steps of reaming the intramedullary canal to accommodate at least a portion of the stem, providing an apparatus having a first clamp, a second clamp, a depth gage and a guide, using the guide to establish the proper rotational orientation of the apparatus, securing the first clamp to the bone, securing the second clamp to the prosthesis, coupling the second clamp to the depth gage, inserting the stem into the intramedullary canal, and reducing the joint.

Other features of the present invention will be apparent to those skilled in the art from the detailed description of the preferred embodiments and the accompanying drawings.

DETAILED DESCRIPTION OF THE PREFERRED EMBODIMENTS

Figure 1:
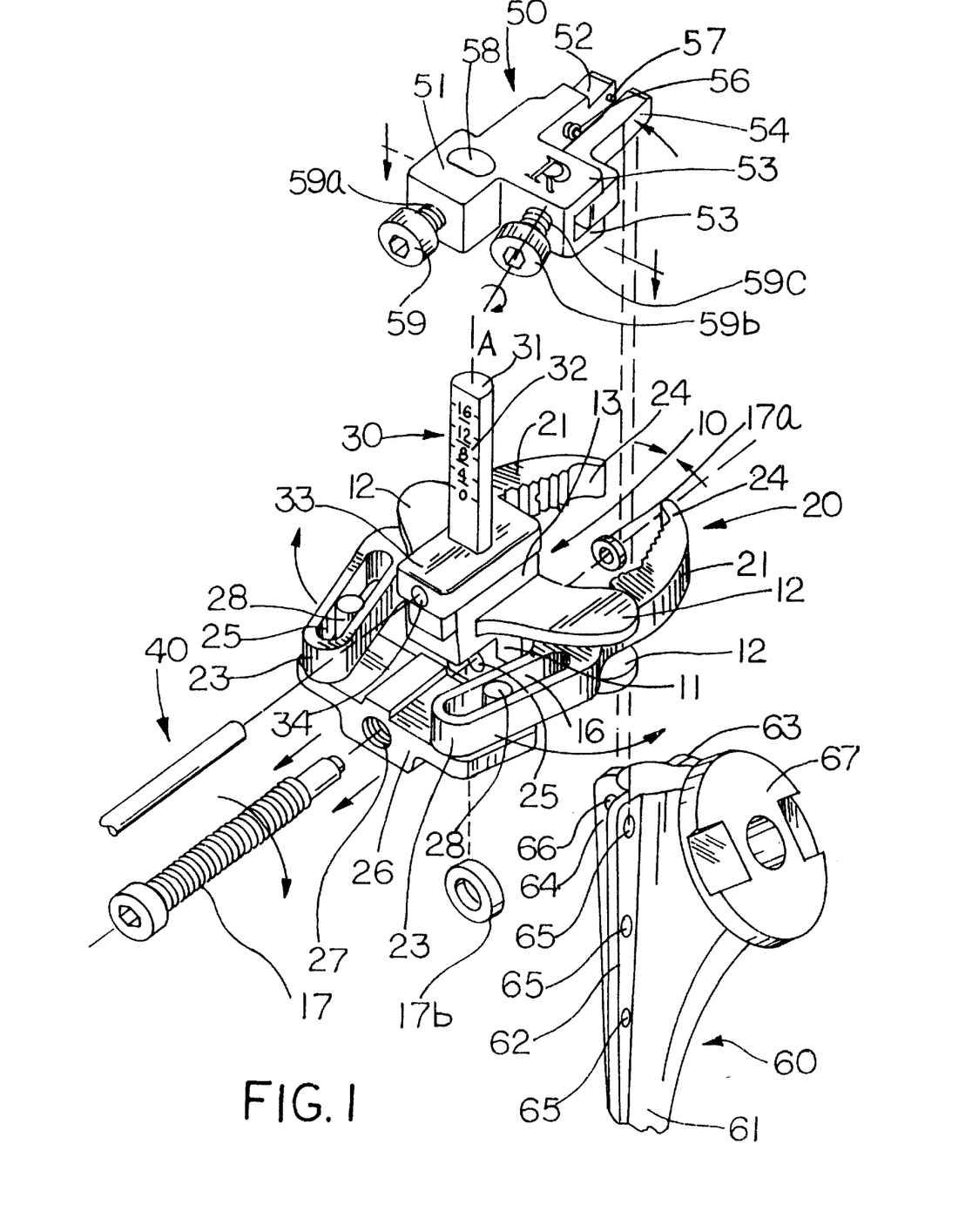
FIG. 1 is an exploded perspective view of an apparatus for positioning a prosthesis in a bone according to one embodiment of the present invention and a humeral prosthesis.
Figure 1A:
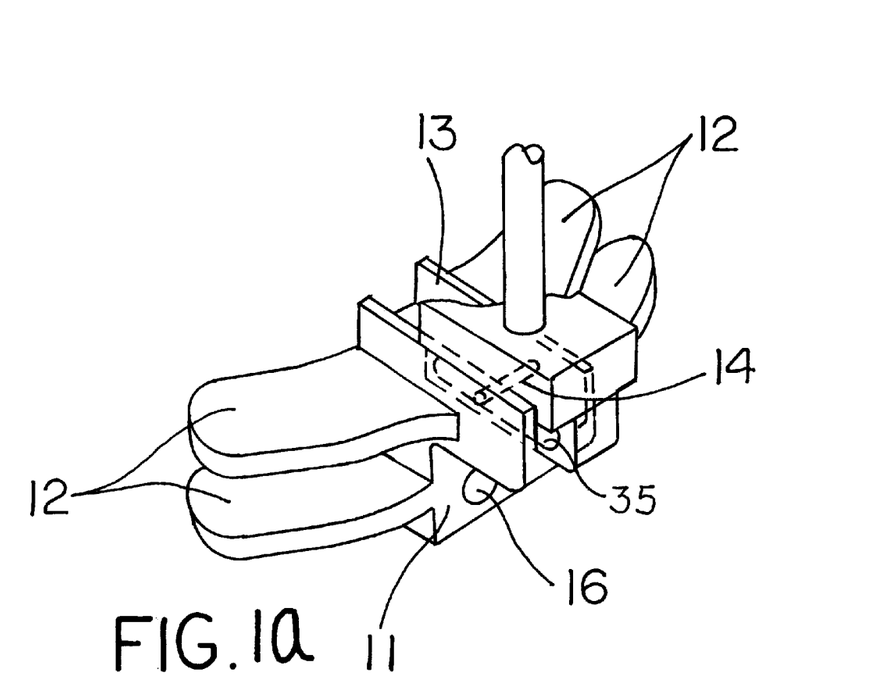
FIG. 1a is a perspective view of a body and depth gage that are components of the apparatus of FIG. 1.

FIG. 1 is an exploded perspective view of an apparatus for positioning a prosthesis in a bone according to one embodiment of the present invention. The apparatus generally includes a body 10, a first clamp 20, a depth gauge 30, a guide 40 and a second clamp 50. Body 10 generally includes a central portion 11 having a pair of spaced-apart arms 12 extending from each side thereof Body 10 further includes a channel 13 having a stop 14 (FIG. 1a) in the form of a post extending across the width of channel 13. A projection 15 extends below channel 13. A bore 16 is formed in body 10 for receiving screw 17 as described below. A pair of washers 17a and 17b are provided for securing screw 17 to central portion 11 of body 10, as described below. Body 10 may be made from any of a number of materials suitable for use in the field of orthopaedic surgery.

Figures 5, 6:
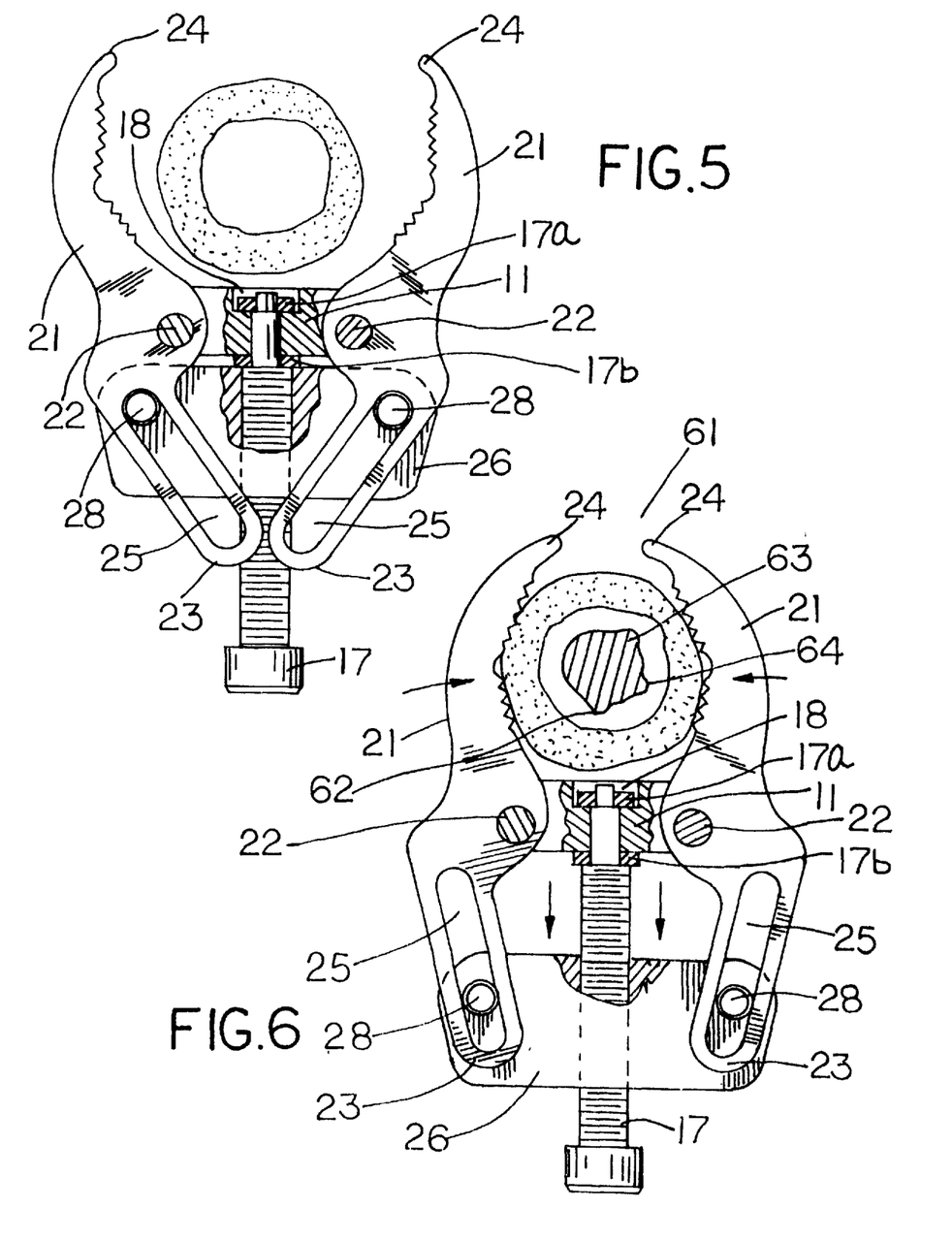
FIG. 5 is a partial cross-sectional, top plan view showing the apparatus of FIG. 1 positioned about a humerus prior to engagement with the humerus.
FIG. 6 is a partial cross-sectional, top plan view showing the apparatus of FIG. 1 engaging a humerus with the prosthesis planted within the intermedullary canal of the bone.
Figure 7:
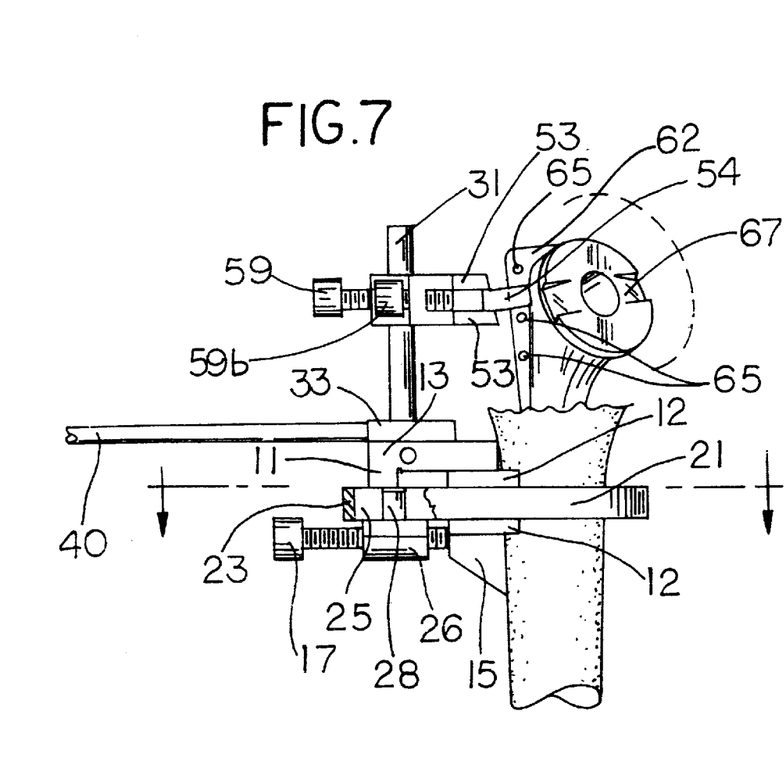
FIG. 7 is a side plan view showing the apparatus of FIG. 1 secured to a humeral prosthesis and a humerus.
Figure 8:
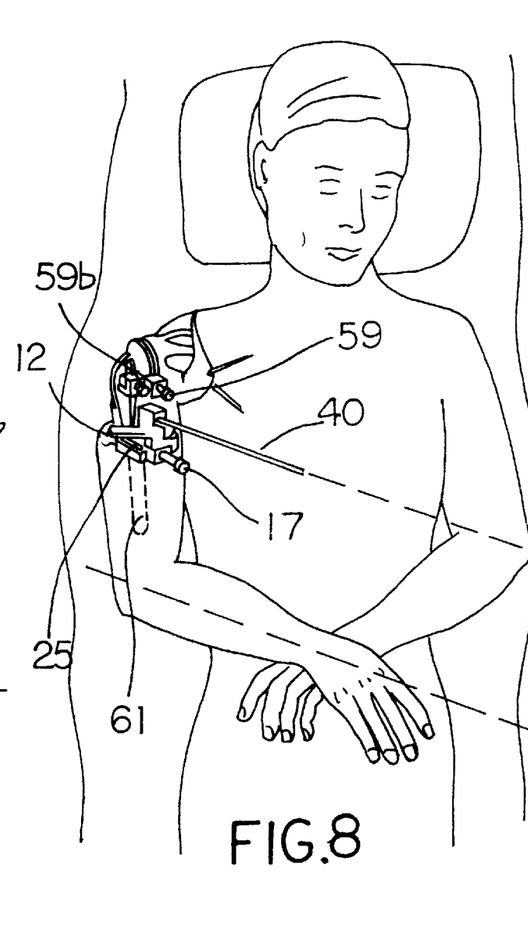
FIG. 8 shows the apparatus of FIG. 1 in use.

First clamp 20 includes a pair of jaws 21 connected to arms 12 by pins 22. This is best shown in FIGS. 5 and 6, wherein the upper arms 12 and part of central portion 11 of body 10 have been removed to better illustrate bore 16, screw 17, washers 17a and 17b and pins 22. Each jaw 21 includes a first end 23 and a second end 24. In the embodiment shown, an opening or slot 25 is formed in each jaw 21 adjacent first end 23. Clamp 20 further includes a cam 26 having a threaded bore 27 therein. Bore 27 receives screw 17 to operate cam 26, as described below. A pair of pins 28 project from cam 26 and are located within openings 25 of jaws 21 as shown. As shown in FIGS. 5 and 6, washer 17a is located within a recessed area 18 of body 10. Washer 17b is located between central portion 11 of body 10 and cam 26. Both washers 17a and 17b are aligned with bores 16 and 27 such that screw 17 can pass through bores 16 and 27 and washers 17a and 17b.

Figure 1B:
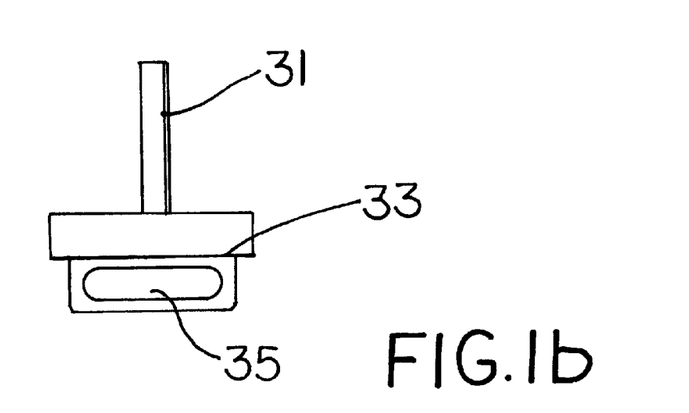
FIG. 1b is a side plan view of a depth gage that forms a component of the apparatus of FIG. 1.

Depth gauge 30, in the embodiment shown, includes a post 31 with a plurality of markings 32 thereon. In the embodiment shown, post 31 has a generally semicircular cross-section transverse to its longitudinal axis A. Post 31 is connected to a base 33 that rides within channel 13 of body 10, as described below. A first opening 34 is located in base 33 for receiving guide 40. A second opening 35 (FIGS. 1a and 1b) is located in base 33 and receives stop 14 located in channel 13 of body 10.

Guide 40, in the embodiment shown, is a rod configured to mate with opening 34 in base 33 of depth gauge 30. Guide 40 can be secured to and removed from base 33 as desired.

Figures 2, 3, 4:
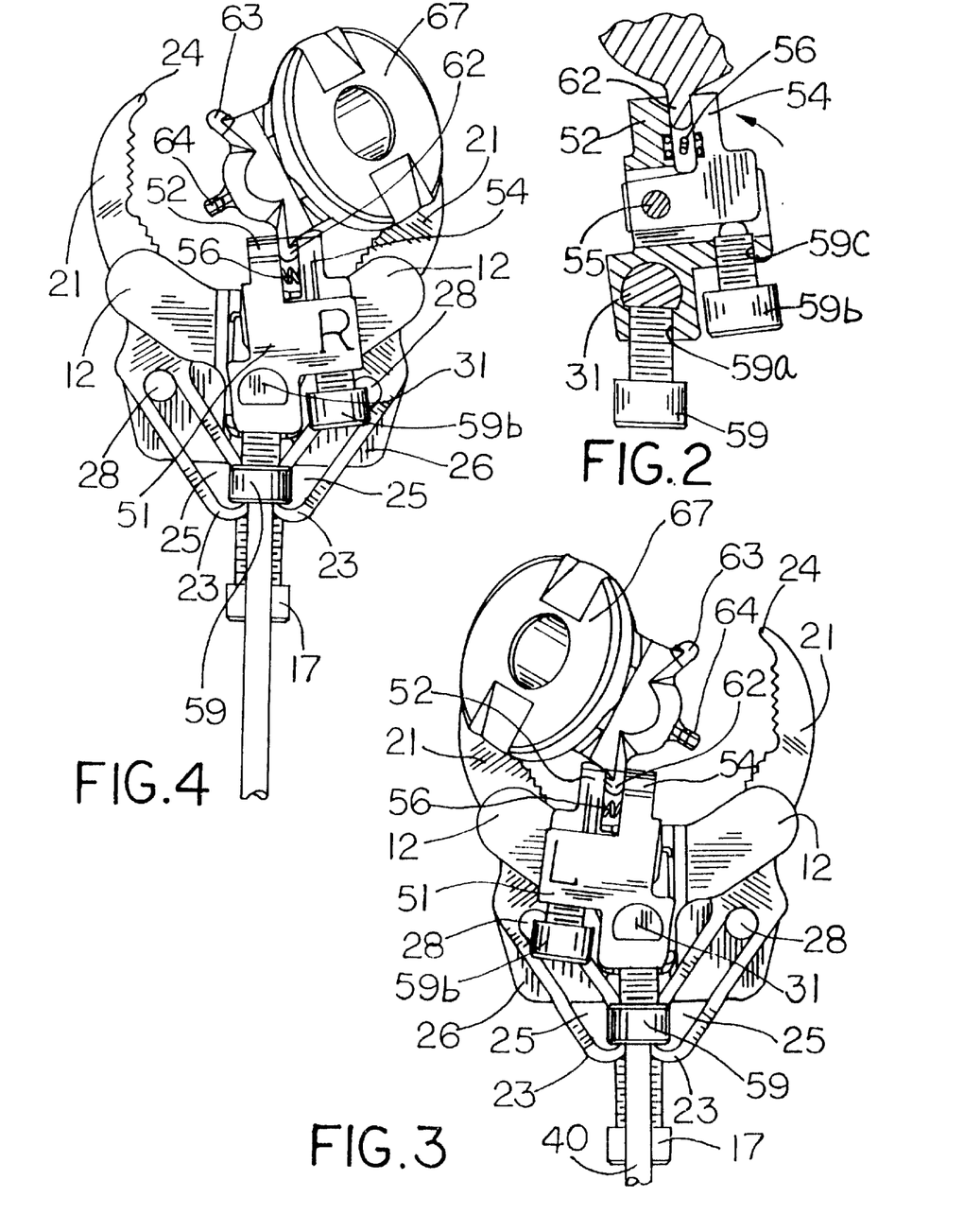
FIG. 2 is a partial cross-sectional view showing a clamp that forms a component of the apparatus of FIG. 1 secured to a humeral prosthesis.
FIG. 3 is a top plan view showing the apparatus of FIG. 1 secured to a prosthesis for use in a left humerus.
FIG. 4 is a top plan view showing the apparatus of FIG. 1 secured to a prosthesis for use in a right humerus.

Second clamp 50 includes a body 51 having a first jaw 52 extending therefrom. Body 51 further includes a pair of spaced-apart arms 53 between which is located a second jaw 54. Jaw 54 is secured to body 51 by a pin 55 so as to be able to pivot with respect to body 51. This is best shown in FIG. 2, where one arm 53 and a portion of jaw 52 have been cut-away to show pin 55. A spring 56 is located between jaws 52 and 54. Spring 56 biases second jaw 54 into an open direction. Jaws 52 and 54 each include a projection 57 on the inner surface thereof. Body 51 further includes an opening 58 configured to engage post 31 of depth gauge 30, as described below. A first screw 59 extends into a threaded opening 59a in body 51 to secure second clamp 50 to depth gauge 30. A second screw 59b extends into a threaded opening 59c to move second jaw 54, as described below. Clamp 50 also includes indicia on body 51 in the form of the letters "R" and "L" to indicated the proper orientation of clamp 50, as described below.

Prosthesis 60 is shown in FIG. 1 as a humeral implant for replacing the proximal end of a human humerus. Prosthesis 60 includes a stem 61 with an anterior fin 62, a posterior fin 63 and a lateral fin 64 extending therefrom. In the embodiment shown, three suture holes 65 are formed in anterior fin 62 and posterior fin 63. A single suture hole 66 is formed in lateral fin 64. Prosthesis 60 further includes a connector 67 for receiving the head portion of the prosthesis.

In use, the humeral shaft is prepared by appropriately surfacing the resected portion of the shaft and reaming the intramedullary canal. The arm is then positioned such that the palm faces anteriorly and the ulna is at a substantially 90° angle to the humerus. Guide 40 is inserted in opening 34 and the apparatus is positioned such that guide 40 is substantially parallel to the ulna. First clamp 20 is then engaged with the shaft of the humerus. This is accomplished by rotating screw 17 with an appropriate tool so as to drive cam 26 in the posterior direction. This causes pins 28 to move within openings 25. As this occurs, pins 28 bear on the inner surfaces of openings 25. The spacing of pins 28 and the orientation of openings 25 is such that cam 26 causes ends 23 of arms 21 to move toward one another. This causes arms 21 to pivot about pins 22 and open at ends 24. Once the apparatus is properly positioned, screw 17 is rotated in the opposite direction to draw cam 26 in the anterior direction. This causes ends 23 of jaws 21 to move away from one another, thereby causing jaws 21 to pivot about pins 22 such that ends 24 approach each other. In this manner, clamp 20 is secured to the shaft of the humerus. Guide 40 may then be removed from opening 34.

Second clamp 50 is then secured to a trial prosthesis. This is accomplished by first orienting second clamp 50 such that the proper indicia, either L for left or R for right, is facing proximally. Screw 59b is then drawn outwardly so that spring 56 will bias jaw 54 away from jaw 52, thereby opening second clamp 50. Second clamp 50 is then positioned such that projections 57 are aligned with the center suture hole 65 on anterior fin 62. Screw 59b is then advanced so as to push arm 54 forward, thereby causing it to pivot about pin 55 and grasp anterior fin 62 such that projections 57 are located within suture hole 65.

The trial is then positioned above the previously reamed intramedullary canal such that stem 61 is aligned therewith and opening 58 in body 51 of second clamp 50 is positioned above post 31 of depth gauge 30 so as to be able to engage post 31. Shaft 61 is then inserted into the intermedullary canal and opening 58 is slid over post 31. When the desired insertion depth is reached, screw 59 is advanced so as to contact post 31 and secure second clamp 50 to depth gauge 30. Note that base 33 of depth gauge 30 can slide back and forth within channel 13 until stop 14 engages either end of opening 35. This allows anterior/posterior positioning of the prosthesis. Note that, in the embodiments shown, the configuration of opening 58 and post 31 are such that opening 58 may engage post 31 in two orientations depending on whether the prosthesis is to be implanted in a right arm or a left arm. Note also that, in the embodiments shown, the trial prosthesis will be oriented with 30° of retroversion if the preceding steps are followed. This is a result of the proper positioning of clamp 20, the orientation and configuration of post 31 and opening 58 and the positioning of anterior fin 62. In the embodiments shown, anterior fin 62 and posterior fin 63 are both positioned at approximately a 60° angle relative to lateral fin 64.

Once the trial is positioned, a trial reduction is performed and the range of motion is checked. Adjustments to the insertion depth and rotational position of the prosthesis may be made as needed. Once the proper insertion depth and rotational orientation are achieved, the position of second clamp 50 relative to markings 32 on post 31 is noted. Screw 59 is then loosened and second clamp 50 is removed from post 31 and the trial prosthesis is removed from the intramedullary canal. Second clamp 50 is then removed from the trial prosthesis and secured to the middle suture hole 65 on anterior fin 62 of the prosthesis to be implanted. The prosthesis is then inserted into the intramedullary canal and opening 58 of second clamp 50 is engaged with post 31. The prosthesis is inserted until second clamp 50 reaches the predetermined location with respect to markings 32 on post 31. Second clamp 50 is then secured to post 31. The prosthesis is now in the predetermined position and may be cemented in place. The apparatus can also be used with prostheses approved for cementless fixation. The apparatus is removed after implantation.

In an alternative method, the humerus is prepared as described above. A trial that includes height indicia that indicate the insertion depth is then inserted into the intramedullary canal. Once the proper depth is reached the height indicators on the trial are noted. The trial prosthesis is then rotated to establish the proper retroversion. The humeral shaft is then notched adjacent the anterior fin to mark the proper retroversion. First clamp 20 is then positioned such that post 31 of depth gauge 30 is aligned with the notch. Clamp 20 is then secured to the shaft of the humerus. Second clamp 50 is then secured to the trial prosthesis and to post 31. Retroversion then may be checked by inserting guide 40 into opening 34 of base 33. If rod 40 is aligned with the forearm as described above, the prosthesis will be automatically at 30° of retroversion. Again, the retroversion can be adjusted as needed. A trial reduction is then performed and the range of motion checked. Once satisfaction orientation of the trial is achieved it is removed and the prosthesis is implanted. This may be done with or without the assistance of the positioning apparatus.

Although the present invention has been described in detail, the same is to be taken by way of example only and not by way of limitation. Numerous changes and modifications may be made to the embodiments disclosed without departing from the spirit and scope of the invention. For example, although use of the apparatus has been illustrated in connection with a shoulder prosthesis, the apparatus, or a slightly modified version, could be used with other prostheses, such as those used in total hip arthroplasty. Also, the predetermined retroversion angle can be changed by altering the relationship between the components. Accordingly, the present invention is to be limited only by the terms of the claims.

What is claimed is:

1. An apparatus for positioning a prosthesis having a stem in an intramedullary canal of a bone, comprising:
    a body;
    a first clamp connected to the body for engaging the bone;
    a depth gage connected to the body; and
    a second clamp connected to the depth gage for engaging the prosthesis;
    wherein said first clamp includes a first pair of jaws which are movable in relation to each other, said first pair of jaws defines a first clamping space therebetween in which said bone is located when said bone is being clamped by said first clamp,
    wherein said second clamp includes a second pair of jaws which are movable in relation to each other, said second pair of jaws defines a second clamping space therebetween in which said prosthesis is located when said prosthesis is being clamped by said second clamp, and
    wherein said depth gage is configured to measure depth of the prosthesis within said intramedullary canal when said bone is clamped within said first clamping space by said first clamp and said prosthesis is clamped within said second clamping space by said second clamp.

2. The apparatus according to claim 1, further including a projection on the body for stabilizing the apparatus when the first clamp engages the bone.

3. The apparatus according to claim 1, further including a guide for determining proper rotational orientation of the apparatus relative to the bone.

4. The apparatus according to claim 3, wherein the guide may be selectively secured to and removed from the body.

5. The apparatus according to claim 1, wherein the second clamp is movable relative to the first clamp.

6. The apparatus according to claim 1, wherein the depth gage is movable with respect to the first clamp.

7. The apparatus according to claim 1, wherein the second clamp is movable relative to the depth gage.

8. The apparatus according to claim 1, wherein the depth gage is movable relative to the body.

9. The apparatus according to claim 1, wherein the second clamp is removable from the depth gage.

10. The apparatus of claim 1, wherein said second clamping space is located linearly above said first clamping space.

11. The apparatus of claim 1, wherein each of said first pair of jaws and said second pair of jaws extends in a generally perpendicular direction in relation to the direction in which said depth gage extends.

12. An apparatus for positioning a prosthesis having a stem in an intramedullary canal of a bone, comprising:
    a body;
    a first clamp connected to the body for engaging the bone;
    a depth gage connected to the body for determining the depth of the prosthesis stem within the intramedullary canal; and
    a second clamp connected to the depth gage for engaging the prosthesis,
    wherein the depth gage is connected to a base, the body includes a channel and the base is movable within the channel.

13. An apparatus for positioning a prosthesis having a stem in an intramedullary canal of a bone, comprising:
    a body;
    a first clamp connected to the body for engaging the bone;
    a depth gage connected to the body for determining the depth of the prosthesis stem within the intramedullary canal; and
    a second clamp connected to the depth gage for engaging the prosthesis,
    wherein the second clamp engages the depth gage in a first orientation for using the apparatus with a bone located on the left side of the body and engages the depth gage in a second orientation for using the apparatus with a bone located on the right side of the body.

14. An apparatus for positioning a prosthesis having a stem in an intramedullary canal of a bone, comprising:
    a body;
    a first clamp connected to the body for engaging the bone;
    a depth gage connected to the body for determining the depth of the prosthesis stem within the intramedullary canal; and
    a second clamp connected to the depth gage for engaging the prosthesis; and
    a cam for adjusting the first clamp.

15. An apparatus for positioning a prosthesis having a stem in the intramedullary canal of a bone having a shaft, the apparatus comprising:

a body;

a first clamp for engaging the bone, the first clamp being coupled to the body;

a depth gage for determining the depth of insertion of the prosthesis stem in the intramedullary canal, the depth gage being coupled to the body and moveable relative to the body in a linear direction toward the shaft of the bone; and a second clamp for engaging the prosthesis, the second clamp being coupled to the depth gage for movement therewith and being movable relative to the body in a first direction generally parallel to the shaft of the bone.

16. The apparatus according to claim 15, further including a cam for operating the first clamp.

17. The apparatus according to claim 15, wherein the depth gage is connected to a base, the body includes a channel and the base is movable within the channel.

18. The apparatus according to claim 17, wherein the base includes a slot and the channel includes a stop for limiting movement of the base.

19. The apparatus according to claim 15, wherein the depth gage includes a post with at least one marking.

20. The apparatus according to claim 15, wherein the second clamp may be connected to the depth gage in at least two orientations.

21. The apparatus according to claim 20, wherein the second clamp may be connected to the depth gage in one orientation for use with a bone on the left side of the patient and a second orientation for use with a bone on the right side of the patient.

22. The apparatus according to claim 15, further including a projection located on the body for preventing the apparatus from tilting relative to the bone.

23. The apparatus according to claim 15, further including a guide for indicating proper rotational orientation of the apparatus relative to the bone.

24. An apparatus for positioning a prosthesis having a stem in the intramedullary canal of a bone, including:

first means for selectively attaching the apparatus to the bone;

second means for determining the depth of insertion of the prosthesis stem in the intramedullary canal, the second means being coupled to the first means;

third means for selectively engaging the prosthesis, the third means being coupled to the second means;

fourth means for permitting movement of the third means relative to the first means in a first direction; and fifth means for permitting movement of the third means relative to the first means in a second direction, wherein the first means includes a clamp, and wherein the first means further includes a cam for operating the clamp.

25. An apparatus for positioning a prosthesis having a stem in the intramedullary canal of a bone, including:

first means for selectively attaching the apparatus to the bone;

second means for determining the depth of insertion of the prosthesis stem in the intramedullary canal, the second means being coupled to the first means;

third means for selectively engaging the prosthesis, the third means being coupled to the second means;

fourth means for permitting movement of the third means relative to the first means in a first direction; and fifth means for permitting movement of the third means relative to the first means in a second direction, wherein the fourth means includes a post and an opening in the third means that engages the post.

26. An apparatus for positioning a prosthesis having a stem in the intramedullary canal of a bone, including:

first means for selectively attaching the apparatus to the bone;

second means for determining the depth of insertion of the prosthesis stem in the intramedullary canal, the second means being coupled to the first means;

third means for selectively engaging the prosthesis, the third means being coupled to the second means;

fourth means for permitting movement of the third means relative to the first means in a first direction; and fifth means for permitting movement of the third means relative to the first means in a second direction, wherein the fifth means includes a body moveable within a channel and the third means is coupled to the body.

27. The apparatus according to claim 26, further including a stop in the channel for limiting movement of the body.

28. A method of implanting a prosthesis having a stem in the intramedullary canal of a bone, comprising the steps of:

reaming the intramedullary canal to accommodate at least a portion of the stem;

providing an apparatus having a first clamp, a second clamp, a depth gage and a guide;

using the guide to establish the proper rotational orientation of the apparatus;

clamping the bone between a first pair of jaws of the first clamp;

clamping the prosthesis between a second pair of jaws of the second clamp;

coupling the second clamp to the depth gage;

inserting the stem into the intramedullary canal; and reducing the joint.

29. The method according to claim 28, wherein the prosthesis is a trial prosthesis.

30. The method according to claim 29, further including the step of removing the second clamp from the depth gage, removing the second clamp from the trial prosthesis, securing the second clamp to an implantable prosthesis, coupling the second clamp to the depth gage and inserting the implantable prosthesis into the intermedullary canal.

31. An apparatus for positioning a prosthesis having a stem in an intramedullary canal of a bone, comprising:

a body;

a first clamp connected to the body;

a depth gage connected to the body; and a second clamp connected to the depth gage and configured to clamp the prosthesis, wherein said second clamp includes a second pair of jaws which are movable in relation to each other, and wherein said second pair of jaws defines a clamping space therebetween in which the prosthesis is located when the prosthesis is being clamped by the second clamp.

32. The apparatus according to claim 31, further including a projection on the body.

33. The apparatus according to claim 31, further including a guide.

34. The apparatus according to claim 33, wherein the guide may be selectively secured to and removed from the body.

35. The apparatus according to claim 31, wherein the second clamp is movable relative to the first clamp.

36. The apparatus according to claim 31, wherein the depth gage is movable with respect to the first clamp.

37. The apparatus according to claim 31, wherein the second clamp is movable relative to the depth gage.

38. The apparatus according to claim 31, wherein the depth gage is movable relative to the body.

39. The apparatus according to claim 31, wherein the second clamp is removable from the depth gage.

40. An apparatus for positioning a prosthesis having a stem in an intramedullary canal of a bone, comprising:
   a body;
   a first clamp connected to the body;
   a depth gage connected to the body; and
   a second clamp connected to the depth gage and connectable to the prosthesis,
   wherein the depth gage is movable relative to the body, and
   wherein the depth gage is connected to a base, the body includes a channel and the base is movable within the channel.

41. An apparatus for positioning a prosthesis having a stem in an intramedullary canal of a bone, comprising:
   a body;
   a first clamp connected to the body;
   a depth gage connected to the body; and
   a second clamp connected to the depth gage and connectable to the prosthesis,
   wherein the second clamp can engage the depth gage in at least two orientations.

42. An apparatus for positioning a prosthesis having a stem in an intramedullary canal of a bone, comprising:
   a body;
   a first clamp connected to the body;
   a depth gage connected to the body;
   a second clamp connected to the depth gage and connectable to the prosthesis; and
   a cam for actuating the first clamp.

43. A method of positioning a prosthesis in an intramedullary canal of a bone, comprising the steps of:
   providing a clamping assembly having (i) a body, (ii) a first clamp connected to said body, (iii) a depth gage connected to said body, and (iv) a second clamp connected to said depth gage;
   clamping said bone within said first clamp;
   clamping said prosthesis within said second clamp; and
   measuring depth of said prosthesis within said intramedullary canal with said depth gage when said bone is clamped within said first clamp and said prosthesis is clamped within said second clamp.

44. The method of claim 43, wherein:
   said first clamp includes a first pair of jaws which are movable in relation to each other, said first pair of jaws defining a first clamping space therebetween in which said bone is located during said bone clamping step, and
   said second clamp includes a second pair of jaws which are movable in relation to each other, said second pair of jaws defining a second clamping space therebetween in which said prosthesis is located during said prosthesis clamping step.

45. A method of positioning a prosthesis in an intramedullary canal of a bone, comprising the steps of:
   clamping said bone between a first pair of jaws of a first clamp;
   clamping said prosthesis between a second pair of jaws of a second clamp; and
   measuring depth of said prosthesis within said intramedullary canal with a depth gage when (i) said bone is clamped between said first pair of jaws of said first clamp, and (ii) said prosthesis is clamped between said second pair of jaws of said second clamp.

\* \* \* \* \*